United States Patent [19]

Murakoshi

[11] Patent Number: 4,519,391

[45] Date of Patent: May 28, 1985

[54] ENDOSCOPE WITH SIGNAL TRANSMISSION SYSTEM AND METHOD OF OPERATING SAME

[75] Inventor: Makoto Murakoshi, Asaka, Japan

[73] Assignee: Fuji Photo Film Co., Ltd., Kanagawa, Japan

[21] Appl. No.: 425,463

[22] Filed: Sep. 28, 1982

[30] Foreign Application Priority Data

Oct. 20, 1981 [JP] Japan .................. 56-167568

[51] Int. Cl.³ .............................................. A61B 17/39
[52] U.S. Cl. .................................... 128/303.15; 128/4
[58] Field of Search ................... 128/303.13, 303.14, 128/303.15, 303.17, 4–8

[56] References Cited

U.S. PATENT DOCUMENTS 3,499,108 3/1970 Simon .................................. 128/6 X
3,942,530 3/1976 Northeved ............................ 128/4 X

FOREIGN PATENT DOCUMENTS 2621321 12/1977 Fed. Rep. of Germany .......... 128/4

Primary Examiner—Lee S. Cohen
Attorney, Agent, or Firm—Birch, Stewart, Kolasch & Birch

[57] ABSTRACT

A signal transmission system for use in an endoscope includes a solid state image sensor for picking up an image of a part of the inside of a cavity of a living body to produce a video signal indicative of the image, a frequency modulator for frequency modulating a carrier frequency with the video signal to produce a frequency modulated signal, video circuitry for receiving the modulated signal to visualize the video signal on a video display, and a transmission circuit for transmitting the modulated signal from the modulator to the video circuitry. A frequency band of the frequency modulated signal is selected outside a frequency band of a noise source including an electrical instrument, such as an electrical scalpel.

16 Claims, 4 Drawing Figures

ENDOSCOPE WITH SIGNAL TRANSMISSION SYSTEM AND METHOD OF OPERATING SAME

BACKGROUND OF THE INVENTION

1. Field of the Invention

The present invention relates to a signal transmission system, and more particularly to such a system for use in an endoscope including a solid state image sensor.

2. Description of the Prior Art

An endoscope has been proposed which employs a solid state image sensor or imaging device, which may be a charge transfer device (CTD), such as a charge coupled device (CCD) and a bucket brigade device (BBD), in the interest of compactness and economy. In general, an imaging device is provided in a viewing head that is to be inserted into a cavity or opening of a living body or machinery to pick up an image of an inside part of the cavity, when driven in a raster scanning fashion, to produce a video signal representative of the image picked up. The video signal is transmitted to a video display device and in turn visualized thereon as a picture indicative of the picked up image.

Endoscopes may often be used under the circumstances where electromagnetic waves are present to such an extent so as to adversely effect noise on video signals produced from an imaging device and transmitted to a video display, causing dots, stripes and smears to appear in a picture displayed.

Specifically in the case of a medical endoscope, an instrument such as a surgical scalpel may be provided in a viewing head to operate on an affected part of a living body. In particular, an electrical scalpel or surgical knife may often be used, which is driven by a high frequency current, which is conducted into an affected part to generate the Joule's heat therein, allowing the cutting out, taking out or incising of the affected part.

A conventional endoscope employing a solid state image sensor together with an electrical instrument such as a high frequency surgical scalpel has a problem that an electromagnetic coupling may occur between an electrical connection associated with the electrical forceps and another electrical connection associated with the image sensor. Specifically, video signals which are analog signals in a baseband produced by the imaging device may often be affected, while transmitted on the electrical connection to a display system, by noise induced from the other electrical connection associated with the electrical forceps, since the electrical connection for transmitting video signals thereon is substantially in parallel in a sheath of the endoscope with the electrical connection for supplying power at a high frequency to the electrical forceps. Consequently, it is difficult to visualize the video signals on a video display as a clear picture suitable for diagnosis of the affected portion. Situation is similar in the case of some industrial fields which are full of electromagnetic waves, as in a welding cite, etc.

SUMMARY OF THE INVENTION

It is therefore an object of the present invention to provide a signal transmission system for use in an endoscope including a solid state image sensor and associated circuitry which are free from the effects of electromagnetic wave sources, such as an electrical forceps, to produce a clear picture indicative of an image picked up by the sensor on a display.

In accordance with the present invention, analog video signals produced from a solid state image sensor modulates a carrier in frequency for transmission, the frequency modulated signals having a frequency band selected outside a frequency band of a driving current for the electrical instrument.

In an aspect of the invention, an image sensor, a frequency modulator circuit and associated circuitry may be shielded electromagnetically.

BRIEF DESCRIPTION OF THE DRAWINGS

Those and further objects and features of the present invention will become more apparent from a consideration of the following detailed description taken in conjunction with the accompanying drawings, in which.

DETAILED DESCRIPTION OF THE PREFERRED EMBODIMENT

Figure 1:
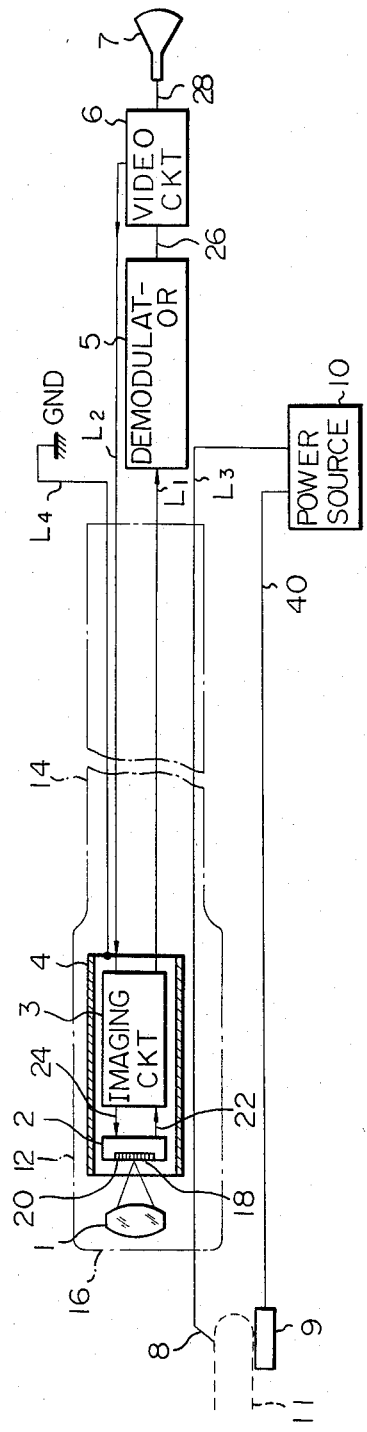
FIG. 1 shows schematically in a block diagram an embodiment of a signal transmission system for use in an endoscope in accordance with the present invention.

FIG. 1 shows an embodiment of a signal transmission system for use in an endoscope having a viewing head 12, which is to be inserted into a cavity or opening of a living body, not shown. Viewing head 12, which is connected with a long tubular, flexible sheath 14 depicted by a chain line with its intermediate portion omitted for simplicity, is equipped at the front or distal end 16 with an objective lens 1 for viewing the inside of the cavity into which the head 12 is inserted. In a focal plane 18 of objective lens 1, disposed is a solid state image sensor or imaging device 2, such as a CTD including a CCD and BBD, to pick up, when driven by a clock signal, an image of a part of the cavity to produce a video signal representative of the picked up image.

Figure 2:
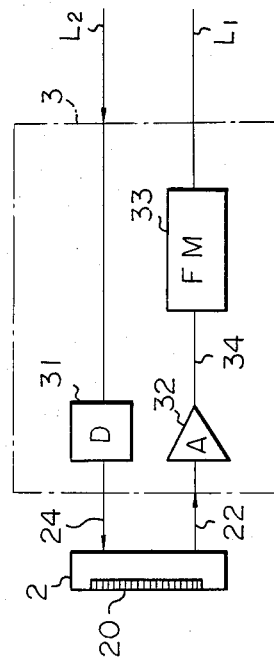
FIG. 2 is a schematic block diagram showing in detail the imaging circuitry included in the system depicted in FIG. 1.

Image sensor 2 has an array of photosensitive cells or pixels 20 disposed in focal plane 18 of lens 1, and is interconnected to imaging circuitry 3 by leads 22 and 24, which circuitry is illustrated more in detail in FIG. 2. Imaging circuitry 3 is interconnected to a demodulator 5 and a video circuit 6, both of which locate outside sheath 14 at the proximal end thereof as shown in the figure, by lines L1 and L2 which run within flexible sheath 14 to the outside thereof.

Figure 3:
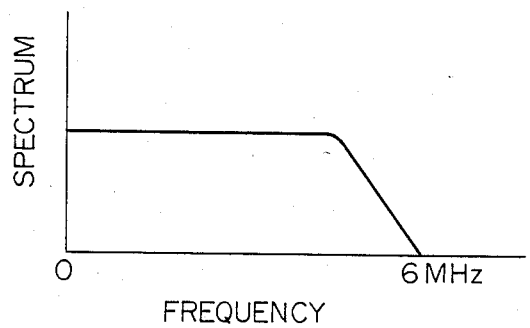
FIG. 3 shows an exemplary frequency spectrum of a baseband video signal produced by the image sensor shown in FIG. 1.

Now referring to FIG. 3, imaging circuitry 3 includes a sensor driver 31 which has an input connected to lead L1 and an output connected to lead 24 to clock or drive imaging device 2 in response to clock or synchronous signals provided from video circuit so as for imaging device 2 to produce in a raster scanning fashion video signals indicative of an image of a portion of the inside of an opening into which viewing head 12 is inserted. Imaging circuitry 3 includes an amplifier 32, which has an input connected to lead 22 and amplifies the video signals produced by sensor 2.

Amplifier 32 has an output 34 connected to an FM modulator 33, which generates a carrier frequency and modulates the carrier in frequency with the video signals coming from imaging device 2 via amplifier 32 to produce frequency modulated (FM) video signals on lead L1, that is connected to an output of modulator 33.

Returning to FIG. 1, demodulator 5 and video circuitry 6 are connected at the proximal end of sheath 14 to leads L1 and L2, respectively. Demodulator 5 receives the FM modulated video signals transmitted over line L1 from imaging circuitry 3 to frequency demodulate them to produce corresponding baseband video signals on its output port 26, which is connected to an input of video circuitry 6.

Video circuitry 6 is adapted to generate clock pulses, which are in turn transmitted over lead L2 to solid state imager 2 via imaging circuitry 3 to drive or clock it in a conventional manner, and to receive the demodulated baseband video signals from demodulator 5 to visualize them on a video display 7, which may be a cathode ray tube (CRT) connected to an output 28 from video circuitry 6.

In the illustrative embodiment, the endoscope includes an electrode 8 which functions as an electrical instrument, such as a surgical scalpel or knife driven by a high frequency current. Electrode 8 is projected from or installed in viewing head 12 and connected to a one terminal of power source 10 by line L3, that runs within sheath 14 substantially in parallel with video signal lines L1 and L2. Power source 10 has the other output terminal 40 connected to the other electrode 9 for the surgical knife, which may be a planar electrode to be in contact with a part 11 of a living body. Power source 10 generates a high frequency current, for example of a frequency ranging generally 300 kHz to 1 MHz to provide electrodes 8 and 9 therewith to generate the Joule's heat in an affected part of the living body to which electrodes 8 and 9 are in contact with for cutting out, taking out or incision.

In operation, image pick up device 2 operates in response to synchronous clocks provided on lead 24 via imaging circuitry 3 from video circuit system 6 to produce in a raster scanning fashion on output lead 22 baseband video signals representative of an image of the opening into which viewing head 12 is inserted. FM modulator 33 receives the baseband video signals on lead 22 to modulate the carrier frequency oscillated therein with the baseband signals to produce the modulated video signals on line L1 to the proximal end of the endoscope. The transmitted signals are received by demodulator 5 to be frequency demodulated into the original baseband video signals, which are in turn amplified by video circuitry 6 to be visualized on CRT 7 as a picture indicative of the picked up image.

In accordance with the present invention, the video signals transmitted over line L1 is essentially free from noise which would be caused by the high frequency current conducted over line L3 from power source 10 because the video signals on lead L1 are carried on a carrier frequency in a frequency modulated fashion.

Figure 4:
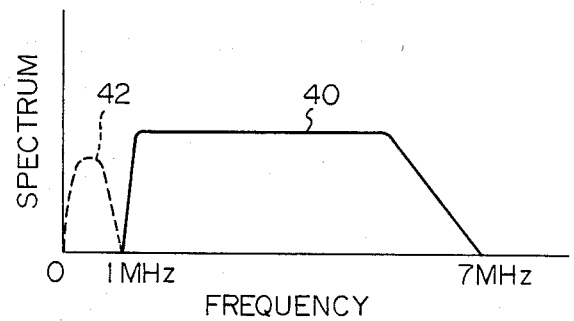
FIG. 4 also shows an exemplary frequency spectrum of a video signal which is frequency modulated on a carrier by the imaging circuitry illustrated in FIG. 1.

In general, the baseband video signals produced from image sensor 2 have a frequency spectrum ranging from d.c. to approximately 6 MHz for a color video system, for example, as plotted in FIG. 3. In accordance with the present invention, FM modulator 33 generates a carrier frequency which is substantially outside the frequency band of the driving current for surgical knife 8, which band ranges from about 300 kHz to 1 MHz, for example. As shown in FIG. 4, FM modulator 33 generates a carrier having a frequency spectrum covering approximately 1 MHz through 7 MHz, depicted by a solid line 40, so that the frequency band between the d.c. component and about 1 MHz is avoided as depicted by a dotted line 42. It is therefore more advantageous for the video signals to be transmitted over lead L1 on a carrier frequency modulated therewith, resulting in a complete freedom from noise that would be caused by the high frequency current on power source line L3 for the electrical scalpel system involved. Accordingly, a clear picture will in turn be produced on a CRT 7 screen without any dots, stripes or smears due to the noise.

In the illustrative embodiment, image sensor 2 and the associated circuitry such as imaging circuit 3 may advantageously be enclosed by an enclosure 4, including or made of an electrically conductive material such as metal, and connected by a lead L4 to a reference potential, e.g. ground GND. Enclosure 4 effectively electromagnetically shields solid state imager 2 and imaging circuitry 3 from noises which would otherwise be induced by an electromagnetic coupling from power supply line L3 running in the vicinity of solid state imager 2 and imaging system 3.

While the present invention has been described in terms of a specific illustrative embodiment, it is to be understood to be susceptible of modification by those skilled in the art within the spirit and scope of the appended claims. For example, imaging circuitry 3 in the illustrative embodiment produces video signals in the direct signal form thereof, but alternatively the imaging circuitry may include, for example, a video matrix network for producing a composite color television signal in accordance with a standard television signalling system, such as the NTSC format.

What is claimed is:

1. An endoscope system having a viewing head connected to an elongated sheath comprising:
   an electrical instrument;
   a high frequency current source electrically connected to said electrical instrument to drive said instrument;
   imaging means provided in said viewing head for picking up an image to produce a video signal representative of the image;
   frequency modulator means interconnected to said imaging means for generating a carrier wave having a frequency band substantially different from a frequency band of the current produced from said current source, said modulator means frequency modulating the carrier wave with the video signal to produce a frequency modulated signal;
   visualizing means responsive to the frequency modulated signal developed by said frequency modulator means for visualizing the video signal by reproducing the picked up image on a display; and
   transmission means provided in said sheath for transmitting the frequency modulated signal from said frequency modulator means to said visualizing means.

2. An endoscope system in accordance with claim 1, wherein, said electrical instrument comprises an electrical scalpel which is driven by the high frequency current.

3. An endoscope system in accordance with claim 2, further comprising shielding means for electromagnetically shielding said imaging means and frequency modulator means from said electrical scalpel.

4. A system in accordance with claim 1, wherein said frequency band of said carrier wave is higher in frequency than the frequency band of said current source.

5. A signal transmission and endoscope system comprising:
an electrical instrument;
a high frequency current source electrically connected to said electrical instrument to drive said instrument;
an elongated enclosure having a viewing head to be inserted into a cavity;
imaging means provided in said viewing head of said elongated enclosure for picking up an image of a part of the inside of the cavity to produce a video signal representative of the image;
frequency modulator means supported by the viewing head and interconnected to said imaging means for generating a carrier wave having a frequency band substantially different from a frequency band of the current produced from said current source, said modulator means frequency modulating the carrier wave with the video signal to produce a frequency modulated signal;
transmission means within the elongated enclosure for transmitting the frequency modulated signal;
frequency demodulator means provided at an end of the elongated enclosure opposite the viewing head thereof for receiving the modulated signal to frequency demodulate the modulated signal into the video signal; and
means responsive to the demodulated video signal for visualizing the demodulated video signal by reproducing the picked up image on a display.

6. A system in accordance with claim 5, wherein said electrical instrument comprises an electrical scalpel which is provided in said viewing head, said system further comprising an electrical connection provided within said enclosure, the high frequency current being supplied over said electrical connection to said scalpel to drive said scalpel.

7. A system in accordance with claim 6, further comprising an additional enclosure of electrically conductive material connected to a reference potential and substantially surrounding said imaging means and frequency modulator means to electromagnetically shield said imaging means and frequency modulator means from said electrical scalpel.

8. A system in accordance with claim 5, wherein said frequency band of said carrier wave is higher in frequency than the frequency band of the current source.

9. An endoscope and scalpel system comprising:
an elongated enclosure having a viewing head to be inserted into a cavity;
a solid state image sensor provided in said viewing head for picking up an image of a part of the inside of the cavity to produce a video signal representative of the image;
an electrical scalpel supported by said viewing head and having an electrical connection over which a driving current of a high frequency is supplied thereto;
high frequency current supplying means connected to said electrical connection for supplying said scalpel with the driving current;
frequency modulator means provided in said viewing head and interconnected to said image sensor for generating a carrier wave having a frequency band substantially different from a frequency band of the current supplied by said current supplying means, said modulator means frequency modulating the carrier wave with the video signal to produce a frequency modulated signal;
transmission means provided within said enclosure for transmitting the frequency modulated signal;
frequency demodulator means provided at an end of the enclosure opposite to said viewing head for receiving and frequency demodulating the modulated signal into the video signal; and
means responsive to the demodulated video signal for displaying the information contained in the video signal on a display.

10. A system in accordance with claim 9, further comprising an additional enclosure of electrically conductive material connected to a reference potential and substantially surrounding said image sensor and modulator means to electromagnetically shield said image sensor and frequency modulator means from said scalpel.

11. A system in accordance with claim 9, wherein said frequency band of said carrier wave is higher in frequency than the frequency band of the driving current.

12. A system in accordance with claim 11, wherein said frequency band of said carrier wave ranges approximately from 1 to 7 MHz.

13. A medical instrument and sensing system comprising:
a medical instrument;
means for supplying high frequency current to said medical instrument;
means for sensing desired image information adjacent to said medical instrument and for producing an output signal indicative thereof;
means for supplying said output signal to a remote location for readout of said information, said means for supplying including,
frequency modulator means responsive to said means for sensing for modulating said output signal to develop a frequency modulated signal, said frequency modulated signal having a frequency band substantially different from the frequency of said high frequency current,
transmission means for transmitting said frequency modulated signal from said modulation means to said remote location,
demodulation means for demodulating said transmitted frequency modulated signal to recreate said output signal indicative of said sensed desired information; and
means receiving said output signal recreated by said demodulation means at said remote location for reading out said sensed information contained therein.

14. The system of claim 13 wherein said frequency band of said modulated signal includes frequencies greater than the frequency of said high frequency current.

15. A method of simultaneously operating a medical instrument supplied with a high frequency drive current and a sensing system comprising:
supplying the medical instrument with a high frequency drive current to drive said instrument;
sensing desired information associated with said instrument and producing an output signal indicative thereof;
supplying said output signal to a remote location by, frequency modulating said output signal to develop a frequency modulated signal, said frequency modulated signal having a frequency band different than the frequency of the high frequency drive current, transmitting said frequency modulated signal to a remote location, demodulating said transmitted frequency modulated signal at said remote location and recovering said output signal; and reading out said sensed information from said recovered output signal.

16. The method of claim 15 wherein each frequency in the frequency band of said frequency modulated signal is higher than the frequency of said high frequency drive current.

* * * * *